(12) United States Patent
Miller et al.

(10) Patent No.: US 8,235,281 B1
(45) Date of Patent: Aug. 7, 2012

(54) LABORATORY SAMPLING MACHINE AND METHODS FOR MAINTAINING CHAIN OF CUSTODY FOR SAMPLES

(75) Inventors: Drew Miller, Flagstaff, AZ (US); Joe Huppenthal, Flagstaff, AZ (US)

(73) Assignee: Merit Automation, LLC, Flagstaff, AZ (US)

( * ) Notice: Subject to any disclaimer, the term of this patent is extended or adjusted under 35 U.S.C. 154(b) by 165 days.

(21) Appl. No.: 12/717,876

(22) Filed: Mar. 4, 2010

Related U.S. Application Data

(63) Continuation of application No. 12/616,783, filed on Nov. 12, 2009, now abandoned.

(60) Provisional application No. 61/114,251, filed on Nov. 13, 2008.

(51) Int. Cl.
*G06F 17/00* (2006.01)
(52) U.S. Cl. ....................................................... 235/375
(58) Field of Classification Search .................. 235/375
See application file for complete search history.

(56) References Cited

U.S. PATENT DOCUMENTS

| | | | |
|---|---|---|---|
| 2002/0150450 A1* | 10/2002 | Bevirt et al. | 414/225.01 |
| 2006/0120835 A1* | 6/2006 | Pressman et al. | 414/331.01 |
| 2009/0155123 A1* | 6/2009 | Williams et al. | 422/65 |

* cited by examiner

*Primary Examiner* — Thien M. Le
*Assistant Examiner* — Christle Marshall
(74) *Attorney, Agent, or Firm* — Coastal Patent Agency; Joshua S. Schoonover

(57) ABSTRACT

A machine and methods for maintaining chain of custody during a sampling procedure is provided, the machine including a sample handling robot having an operation head and a verification head. The verification head can be one of a barcode reader, OCR scanner, of RFID tag reader. The verification head of the machine is adapted to read a sample container prior to sampling an aliquot of liquid, and transferring the aliquot to a testing vial. Each sample container and corresponding testing vial is read prior to performing an operation, such that a chain of custody is properly recorded. The machine can further comprise a secondary robot for improved operation.

20 Claims, 9 Drawing Sheets

LABORATORY SAMPLING MACHINE AND METHODS FOR MAINTAINING CHAIN OF CUSTODY FOR SAMPLES

CROSS-REFERENCE TO RELATED APPLICATIONS

This application is a CON of U.S. patent application Ser. No. 12/616,783, which relates to Provisional Application Ser. No. 61/114,251 filed Nov. 13, 2008, the entire contents of which are hereby incorporated by reference.

FIELD OF THE INVENTION

The present invention relates to a laboratory sampling machine, and more specifically to a machine and methods for high-throughput sample processing for use in laboratory testing and related applications.

BACKGROUND OF THE INVENTION

Demand for laboratory tests; including drug and alcohol tests, blood sugar level tests, and others, has steadily increased as these tests have gained wide acceptance in the medical field, law enforcement, and employment screenings. Until recently, the entire procedure for collecting, preparing and testing samples was limited to the speed and accuracy of trained personnel. However, within the last decade, laboratories and other testing facilities have trended towards at least a partially automated process, and have incorporated the use of machinery to assist in the preparation and testing of samples.

Prior to the introduction of automated machines into the field, a user would deposit a sample of urine, blood or other bodily fluid into a sample container. The sample container would be sealed by a medical professional, usually with a tamper-evident tape, and transferred to a laboratory for measurement and analysis. Once the sample container is received in the laboratory, caution is taken to ensure that the sample container remains sealed, such that unwanted contaminants are prevented from entering the sample container. A laboratory technician would then open each sample container, individually, and introduce an aliquot of the sample to a testing vial for processing in an analytical testing machine.

Because this system was subject to human errors, testing results were often subject to inaccuracies resulting from mislabeling, cross-contamination, and others. Human technicians are subject to fatigue, attention-span limitations, physical limitations, and other limitations which have been shown to reflect on an increased error percentage, especially as duration of a shift is increased. As requirements for testing increase, technicians were required to work longer shifts, and in turn, an increase in errors became prevalent in the industry.

Recently, there has been a trend towards automated machinery for processing and testing samples in the laboratory. U.S. Pat. No. 6,531,096, filed Oct. 6, 1998, and entitled "METHOD AND APPARATUS FOR AUTOMATICALLY OPENING AND CLOSING VIAL LIDS", herein referred to as the '096 patent, discloses one automated solution for opening tamper-sealed vials and sampling the contents thereof, the entire contents of which are hereby incorporated by reference.

Although the '096 patent provided a solution for minimizing human errors and increasing throughput of samples by automating portions of the testing process, several problems remain yet to be solved.

In the laboratory sampling and testing industry, there is a continued need for reducing sample-to-sample cross-contamination, and environment-to-sample cross contamination. The embodiments described in the '096 patent provide a sample station immediately adjacent to the testing vial station, therefore failing to sufficiently isolate the opening of sample containers from testing vials. This system has a significant potential for cross-contamination of samples.

Another limitation with the embodiments disclosed in the '096 patent relates to machine malfunctions, or jams. Under the embodiments disclosed in the '096 patent, a machine jam requires an operator to remove each of the vials from the rack, fix the machine malfunction, and then replace the vials, therefore causing a concern for cross contamination. It would be beneficial to provide a machine adapted to process each sample independently, such that the need to remove sample containers and testing vials, and corresponding risks for cross contamination are eliminated.

The embodiments of the prior art, including the '096 patent, require the use of a scoring member to score the tamper-evident tape maintaining the sample containers in a closed position. The scoring allows the machine to open the sample containers for processing. Without scoring the tamper-evident tape, machines of the prior art are unable to effectively open the sample containers. It would be beneficial in the art if the current requirement for scoring tamper-evident tape was eliminated, such that the time require to process samples can be decreased, and high-throughput of samples can be achieved efficiently.

Input and Output buffers, i.e. conveyors for positioning sample racks, as disclosed in the '096 patent, are inherently troublesome and contribute to additional risks for machine failures, or jams. For example, in the laboratory environment a technician must take caution for placing objects near moving parts. Technicians have been known to set objects on machines, such as pens and pencils, papers, clip boards, sample containers, and other objects. The conveyors, which move at time-delineated intervals, may periodically appear to be stationary, and a technician may set an object on the machine conveyor. Alternatively, a foreign object may land on the conveyor or after a period of time a spill or other object may collect on the conveyor, such that the conveyor eventually malfunctions, and causes the machine to jam. Fewer moving parts exposed to the operator would minimize risks associated with machine malfunctions, and ultimately cross-contamination. Additionally, conveyor belts tend to stretch over time and eventually lead to mechanical malfunctions. Therefore, it would be beneficial to provide a machine that uses fewer exposed moving parts, such as conveyors, such that risks for mechanical errors and contamination are sufficiently minimized.

Another limitation to automated sampling machines as currently known and described in the prior art, relates to the size of the machines. For example, as described in the '096 patent, the prior art embodiments require a first station to transfer aliquots from each sample container to a vial, and multiple other stations. These machines are required to move the sample to various stations for performing several functions. The additional stations require a sizable area for operation. As is understood by one having skill in the art, laboratory space is expensive and often limited. Large machines are therefore discouraged. Additionally, the excess power used by larger machines, especially those machines having multiple stations for activity, is of concern. It would be an improvement in the art if a machine were provided which could process samples under the requirement for smaller floor, or bench top space. It would be an additional benefit if the machine were capable of high-throughput sampling while consuming less power, and further beneficial if a robot were provided for transferring samples such that the sample containers remain in a stationary position.

Further limitations in the art include machines having multiple barcode readers fixedly disposed throughout multiple stations of the machine. Here, a robot would pass by a barcode reader at a fixed location, and a read would be performed such that information is recorded. One problem with these machines includes the cost associated with the several barcode readers, the maintenance involved with the system of barcode readers, and the added space and power requirements of the machine.

The inventors of the present invention recognized that if would be of further benefit to provide samples that are tracked at each stage of the collection, preparation, and testing process, such that results can be quality controlled and assured, this is referred to in the art as Chain of Custody (COC). Currently available machines do not maintain a proper chain of custody. It would be beneficial to the art if a machine were provided being capable of separately processing each sample, such that a chain of custody can be accurately recorded.

In sum of the foregoing problems and limitations of prior art equipment, it would be beneficial to provide a machine for processing laboratory samples, the machine being capable of automated processing such that high-throughput of samples can be achieved. It would be further beneficial to provide a machine capable of opening sample containers individually, and in a region where no other sample containers or testing vials can be exposed to spillage, such that risks for cross-contamination are eliminated. It would be beneficial to provide a machine which processes each sample individually, such that upon a machine malfunction, the integrity of a single sample can be inspected in isolation from other samples. It would be beneficial to provide a machine capable of opening sample containers without the need for a scoring object, such that sample processing time is decreased and machine space and power requirements are conserved. It would further benefit the art if a machine were provided having fewer exposed moving parts, such that machine malfunctions and resulting contaminations can be minimized. It would be beneficial in the art to provide a machine requiring smaller floor or bench-top space. It would be beneficial to provide a machine for processing samples while consuming less power. Finally, it would be beneficial to provide a machine which processed samples individually, and recorded data associated with each step of the process, such that Chain of Custody can be recorded and subsequently verified in compliance with a quality protocol.

SUMMARY OF THE INVENTION

It is therefore an object of the present invention, to solve these and other problems in the art by providing a machine and methods for processing laboratory samples, the machine including a sample-handling robot for transferring a sample aliquot from a sample container to a testing vial; the sample-handling robot further including a verification head for reading and recording an identification member of the sample container and testing vial, the machine therefore maintaining a verifiable chain of custody to ensure the integrity of each sample tested. In the embodiments of the invention, the sample-handling robot includes an operation head for performing one of a number of possible operations with a given sample; and a verification head for identifying and recording sample information with a computerized database.

In one embodiment, the machine includes a sample-handling robot having an operation head and a verification head, a sample container opening device positioned at a first station, and a second station for transferring a sample to one or more testing vials. The machine can further comprise a tip station for providing a rack of plastic pipette tips, or other tips for sampling liquids. The machine further comprises a waste receptacle at a waste station, the waste receptacle adapted to receive used tips and sample fluids.

A user first places a sample into the sample container opening device located at the first station of the machine. The sample-handling robot translates horizontally to a position above the tip station, and the operation head subsequently translates vertically to accept a tip before retracting back to a home position. The sample-handling robot then translates horizontally within an xy-plane to the first station in preparation of receiving a sample aliquot. The verification head translates vertically along a z-axis to a position proximate to the sample, and reads a label positioned on an exterior surface of the sample before returning to a home position. The lid opening device then rotationally actuates the lid of a sample container to an open position and the operation head translates vertically from the home position to a position proximate to the sample. The operation head performs an operation, such as an aspiration to withdraw an aliquot of the sample into the tip. The sample-handling robot then translates to the second station at a position above a testing vial. The verification head translates vertically to a position proximate to the testing vial, and reads a label positioned on the exterior surface of the testing vial before retracting to a home position. The operation head then translates vertically from the home position to a position proximate to the testing vial, and an aliquot of the sample is transferred to the testing vial before the operation head returns to the home position. The sample-handling robot then translates to the waste receptacle station and ejects the used tip into the waste receptacle before translating to the tip station to prepare for a subsequent transfer. The process is repeated for a number of samples.

The verification head can include a barcode reader, an optical character recognition (OCR) reader, or a radiofrequency identification (RFID) tag reader. Similarly, the sample containers can be configured for use with the verification head, such that where the verification head is a barcode reader, an optical character recognition (OCR) reader, or a radiofrequency identification (RFID) tag reader, the sample container includes a barcode, character label, or RFID tag, respectively. In addition, the testing vials can include a barcode, character label, or RFID tag, such that the verification head is adapted to read the testing vials. The barcode, character label, or RFID tag can be commonly referred to herein as an identification member.

The operation head, and the verification head of the sample-handling robot can include a rack and pinion system driven by a motor, such as a stepper motor or other motor, for providing vertical translation in a z-axis direction. The sample-handling robot is configured to translate the operation head and the verification head horizontally within a Cartesian xy-plane, and vertically along a z-axis. Each of the operation head, and the verification head, is adapted to vertically translate independently of the other.

In another embodiment, the operation head is adapted for vertical translation as described above, and the verification head is fixedly positioned at a distance from the sample-handling robot. The verification head can be fixedly positioned above the corresponding identification member of a sample container, or testing vial. Alternatively, the verification head can be fixedly positioned adjacent to the identification member of a sample container, or testing vial. Furthermore, the verification head can be fixedly positioned on the robot and move with the robot to one or more positions proximate to the corresponding identification member of a sample container, or testing vial.

In another embodiment, the verification head can be mechanically coupled to a linear or rotary pneumatic actuator, linear servomotor, a manually operated guide, retractable linkage, pivoting arm, or the like for positioning and rotation about the z-axis.

In yet another embodiment, a secondary robot is provided in addition to, or instead of a sample handling robot. The secondary robot is adapted to translate within a xy-plane, and to retractably translate in a vertical z-axis direction. The secondary robot can be adapted to grip and transport objects, such as sample containers or testing vials, among a variety of stations; for example a lid-opening station, an aliquot sampling and transfer station, and others.

Other embodiments of the invention will become apparent to one having skill in the art upon review of the forgoing description in combination with the detailed description and the drawings provided herein.

BRIEF DESCRIPTION OF THE DRAWINGS

These and other attributes of the invention will become more clear upon a thorough study of the following description of the invention, particularly when reviewed in conjunction with the drawings, wherein.

DETAILED DESCRIPTION OF THE INVENTION

Figure 1:
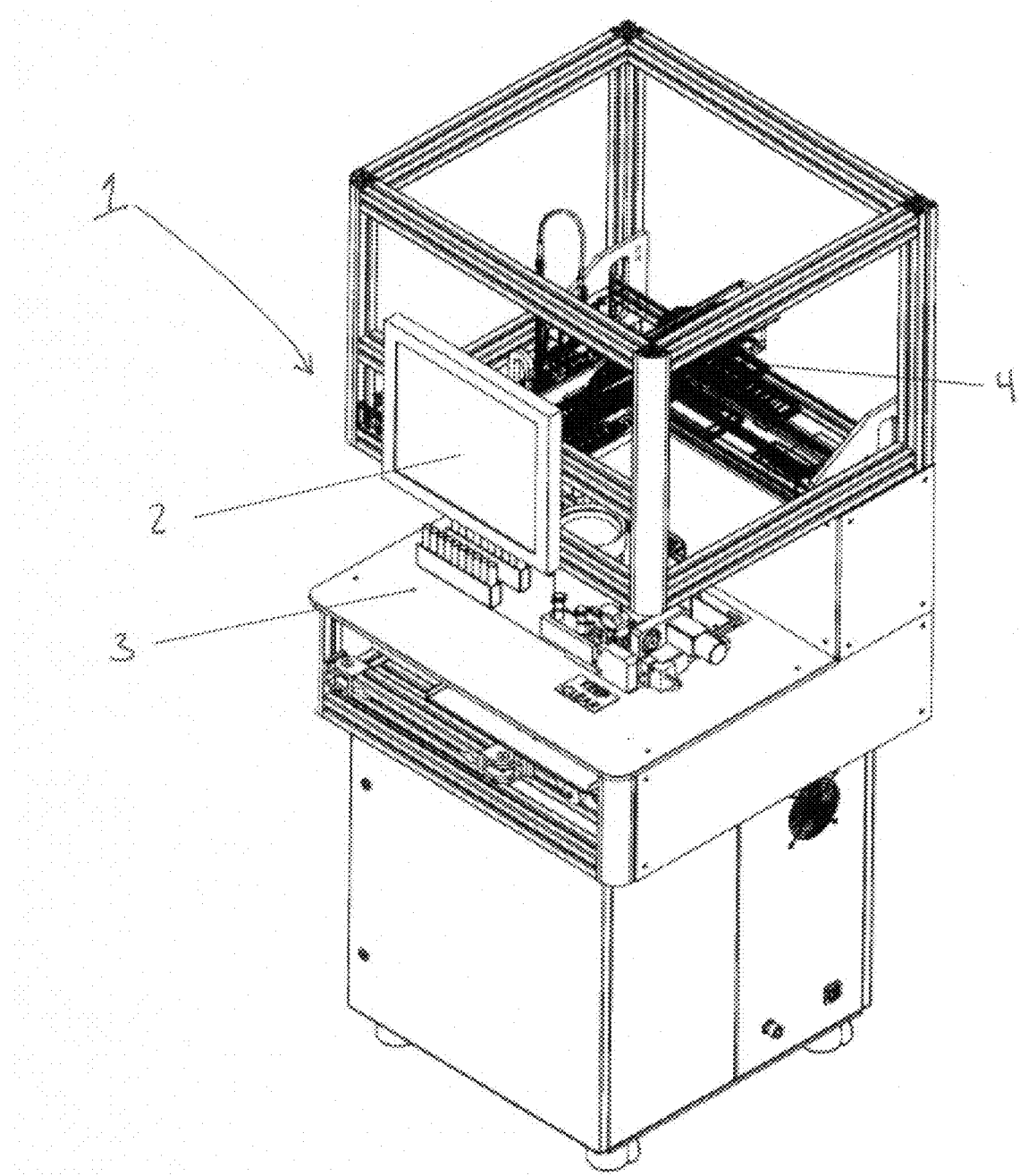
FIG. 1 is a perspective view of a machine for processing samples according to one embodiment of the invention.

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention. Certain embodiments will be described below with reference to the drawings wherein illustrative features are denoted by reference numerals.

Sample-Handling Robot with Translational Verification Head

In one embodiment, a laboratory sampling machine is provided, the machine comprising a sample handling robot having an operation head and a verification head, and an operation platform having a first station for receiving a sample container and a second station for transferring an aliquot of sample liquid to a testing vial.

The sample-handling robot can be any robot adapted to process liquid samples, fine powders, high-density vapors/gases and biologic materials.

The operation head of the sample-handling robot can include a pipette member connected to a length of tubing. The pipette member can be pneumatic or hydraulically driven. The pipette member is adapted to receive a tip, such as a sterile pipette tip. The pipette member includes an elongated tubular body which extends vertically through the distal support bar of the sample-handling robot. The pipette member is adapted to vertically translate from an operation head home position, where the pipette member is at a maximum height above the operation platform, to a position proximate to one of a sample container, or a testing vial. For purposes of the invention, an operation home position is realized when the pipette member of the operation head is at a maximum distance above the operation platform.

The verification head of the sample-handling robot includes one of a barcode reader, optical character recognition (OCR) reader, or a radiofrequency identification (RFID) tag reader. The verification head can be mechanically coupled to a rack and pinion system for providing vertical translational movement; the rack and pinion system is driven by a motor, such as a stepper motor or other motor. Alternatively, the verification head can be fixedly positioned at a distance above the operation platform. The verification head is adapted to recognize and record data associated with an identification member upon performing a read operation. The verification head is said to be at a verification-home position where the verification head is at a maximum distance above the operation platform. The verification head can translate vertically to a position proximate to the identification member of a sample container, or a testing vial.

The identification member generally includes one or more of: a barcode, alpha-numeric character label, or a radiofrequency identification (RFID) tag. Depending on the verification head selected for operation, a corresponding identification member is recommended; for example, a barcode reader is the preferred verification head for use with sample containers and vials having a barcode identification member. The identification member is positioned on an exterior surface of one or more sample containers and testing vials.

The first station of the operation platform includes a sample receiving member, and a sample container lid-opening device. The sample receiving member can be any rack or other object designed to receive and maintain a sample container in an upright position. The lid-opening device comprises a motor and a lid-gripping member, the lid-gripping member is positioned above a sample container lid. Upon activation of the motor, the lid-opening device rotationally actuates the lid of the sample container from a closed to an open position, such that the contents of the sample container become available to the operation head of the sample-handling robot.

The second station of the operation platform includes one or more testing vials positioned in a rack. The rack comprises a number of slots ($n_1$) disposed along an x-axis direction. The rack holds up to ($n_1$) testing vials at the second station of the machine. Each rack, or row of testing vials, can be separated by a gap, such that the verification member can translate to a position proximate to the identification member of each testing vial without contacting the vials.

The machine can further include a tip station for including a rack of tips for use with the operation head of the sample-handling robot. The tips can comprise sterile tips, such as plastic pipette tips and similar tips for aspirating liquid samples as known in the art.

The machine further includes a waste receptacle station having a waste receptacle for receiving ejected tips and sample purges. The waste receptacle can be a substantially cylindrical tube extending vertically from a bottom surface of the operation platform. Alternatively, the waste receptacle can be any shape adapted to receive used tips and sample purges. The waste receptacle can be removable from the operation platform, or alternatively the waste receptacle can include a tubular pathway for directing waste tips and sample liquids to a bin, receptacle, or other waste capture member. The machine may further include one or more carboys for providing deionized (DI) water or other liquid for purging the lines of the operation head.

A second waste station can be provided with the machine, the second waste station including a waste receptacle for collecting liquids disposed during a purge of the sample-handling robot. The waste receptacle of the second waste station can be connected to a waste collection member by a length of tubing, or other method known in the art.

A method of maintaining a chain of custody throughout a processing sequence comprises the steps of: (a) placing a first article into a first station, the first article including an identification member; (b) translating a verification head from a verification-home position to a position proximate to the first article; (c) reading the identification member of the first article; (d) returning the verification head from a position proximate to the first article to the verification-home position; (e) translating an operation head from an operation-home position to a first operation position proximate to the first article; (f) performing a first operation on the first article using the operation head; (g) translating the operation head from the first operation position proximate to the first article to the operation-home position; (h) translating the verification head and the operation head to a second station having a second article, the second article including an identification member; (i) translating the verification head from the verification-home position to a position proximate to the second article; (j) reading the identification member of the second article; (k) translating the verification head from a position proximate to the second article to the verification-home position; (l) translating an operation head from an operation-home position to a second operation position proximate to the second article; (m) performing a second operation on the second article using the operation head; (n) translating the operation head from the second operation position proximate to the second article to the operation-home position.

The method of maintaining a chain of custody throughout a processing sequence can further comprise the steps of: (o) translating the verification head and the operation head to a third station having a third article, the third article including an identification member; (p) translating the verification head from the verification-home position to a position proximate to the third article; (q) reading the identification member of the third article; (r) translating the verification head from a position proximate to the third article to the verification-home position; (s) translating an operation head from an operation-home position to a third operation position proximate to the third article; (t) performing a third operation on the third article using the operation head; (u) translating the operation head from the third operation position proximate to the third article to the operation-home position.

The first, second, and third articles can comprise containers. The first article can contain a sample, such as a biological sample, liquid sample, product sample, or any other sample. The second article can comprise a testing vial for receiving an aliquot of the sample from the first article. In one embodiment, the second article is a testing vial having an identification member positioned on an exterior surface, and the first article is sample container comprising a biological sample. The sample-handling robot is adapted to withdraw an aliquot of the biological sample from the sample container and transfer the aliquot to the testing vial. The testing vial is then processed with an analytical device.

Sample-Handling Robot with Fixed Verification Head

In another embodiment, a laboratory sampling machine is provided, the machine comprising a sample handling robot having an operation head and a verification head, and an operation platform having a first station for receiving a sample container and a second station for transferring an aliquot of sample liquid to a testing vial. The verification head is positioned at a fixed vertical distance from the sample handling robot. The machine is adapted to include testing vials positioned in rows, wherein a gap is formed between rows, the gap including a distance greater than the width of the verification head such that the verification head is adapted for translational movement between rows of testing vials without contacting the vials.

In this embodiment, other features of the machine are adapted to accept the fixedly positioned verification member. For example, the robot can be programmed to move along clear and unobstructed pathways. The waste receptacle station can be positioned lower than the verification head, such that the operation and verification heads can freely pass above the waste receptacle station without contacting the waste receptacle.

Plurality of Sample-Handling Robots with Verification Heads

In another embodiment, the laboratory sampling machine comprises two or more sample handling robots. Each of the sample handling robots can be configured with a separate verification head to include one of: a barcode reader, optical character recognition (OCR) reader, or a radiofrequency identification (RFID) tag reader.

Secondary Robot with Verification Head

In yet another embodiment, a laboratory sampling machine is provided, the machine comprising a secondary robot having an operation head and a verification head, and an operation platform having a first station for receiving a sample container and a second station for transferring an aliquot of sample liquid to a testing vial.

In this embodiment, the operation head includes a first gripping member, and a second gripping member, the first and second gripping members adapted for mechanical actuation, such that the first gripping member and second gripping member can clamp an article, vertically translate the article to a position above the operation platform, translate the article to a position in the xy-plane, vertically return the article to the operation platform at a station, and release the article. This setup is generally descriptive of an operation head for a pick-and-place robot. Various methods for providing an operation head of a secondary robot will become apparent to one having skill in the art.

In other embodiments, the operation head can include various components known in the art, therefore a secondary robot can be any robot; other than a sample-handling robot, known and used in the art for automating a process. One example of a secondary robot includes a pick-and-place robot as described above.

In the same embodiment, the verification head includes one of a barcode reader, optical character recognition (OCR) reader, or a radiofrequency identification (RFID) tag reader. The verification head is mechanically coupled to a rack and pinion system for providing vertical translational movement; the rack and pinion system driven by a motor, such as a stepper motor or other motor. The verification head is adapted to recognize and record data associated with an identification member upon performing a read operation.

Alternatively, the verification head can be configured at a fixed distance from the secondary robot, as is described above, where the verification head rests at a height above the operation tray such that as the verification head translates to a position proximate to a sample container or testing vial having an identification member, the verification head may perform a read of the identification member.

The identification member generally includes one or more of: a barcode, alpha-numeric character label, or a radiofrequency identification (RFID) tag. Depending on the verification head selected for operation, a corresponding identification member should be used; for example, a barcode reader is the preferred verification head for use with sample containers and vials having a barcode.

Combination of Sample-Handling and Secondary Robots having Verification Heads

In another embodiment, a laboratory sampling machine is provided, the machine comprising a sample handling robot having a first operation head and a first verification head, a secondary robot having a second operation head and a second verification head, and an operation platform having a first station for receiving a sample container and a second station for transferring an aliquot of sample liquid to a testing vial. The secondary robot is adapted for selecting a sample for testing and transferring the sample to a station for processing. The sample handling robot is adapted to perform aspiration and dispensing operations with a sample.

In this embodiment, the first verification head, and second verification head are independently selected from the group consisting of: a barcode reader, optical character recognition (OCR) reader, or a radiofrequency identification (RFID) tag reader. The first operation head is a sample-handling operation head, such as a pipette or other liquid-aspiration device. The second operation head can be a pick and place operation head, such as a mechanical gripping device.

Figure 2:
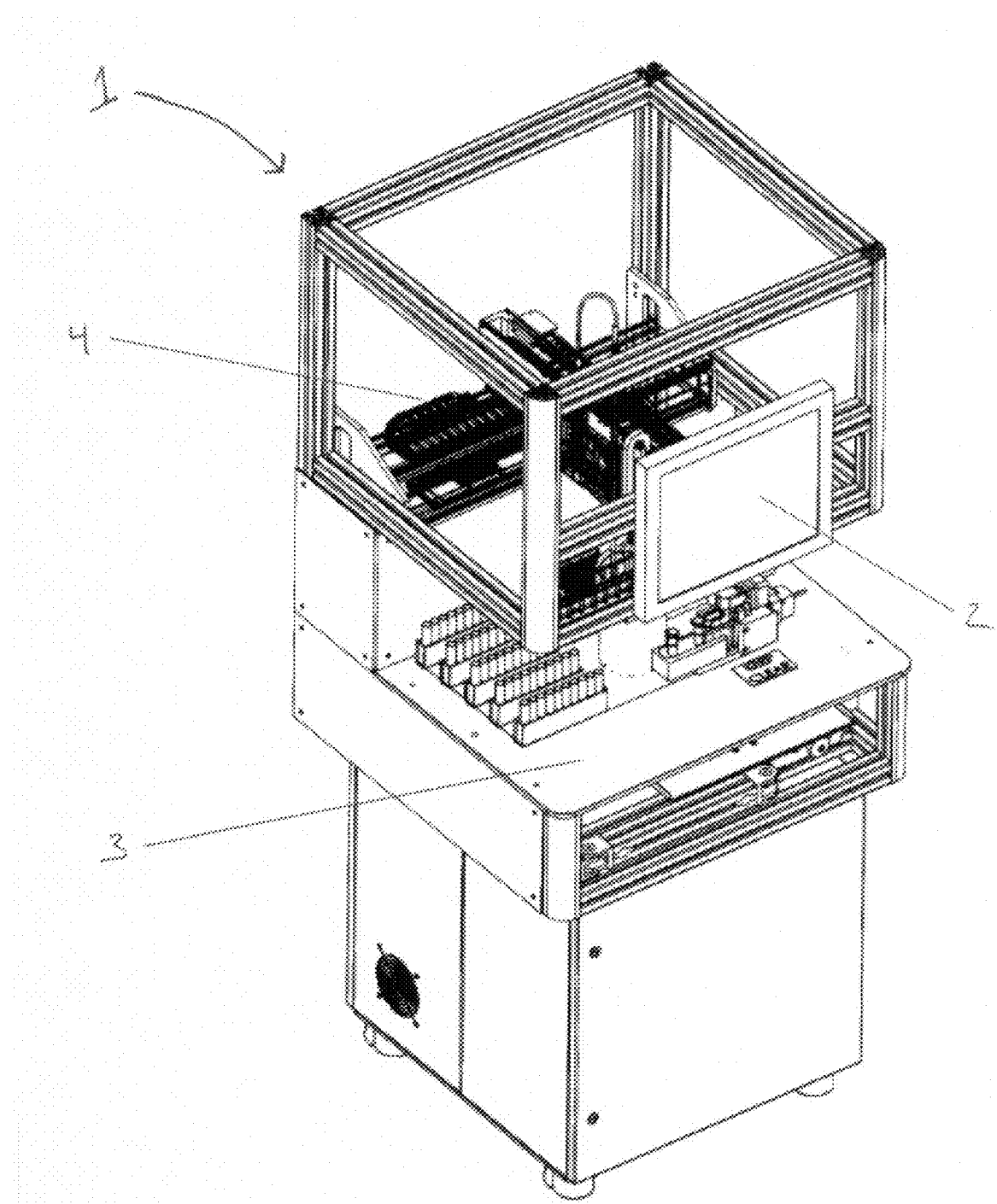
FIG. 2 is a perspective view of a machine for processing samples according to one embodiment of the invention.

As illustrated in FIGS. 1-2, a machine 1 is provided comprising a sample handling robot 4, and an operation platform 3 having a first station 7 for receiving a sample container and a second station 8 for transferring an aliquot of sample liquid to a testing vial. A monitor 2 is provided for displaying information and data relating to samples at each stage of the process.

Figure 3:
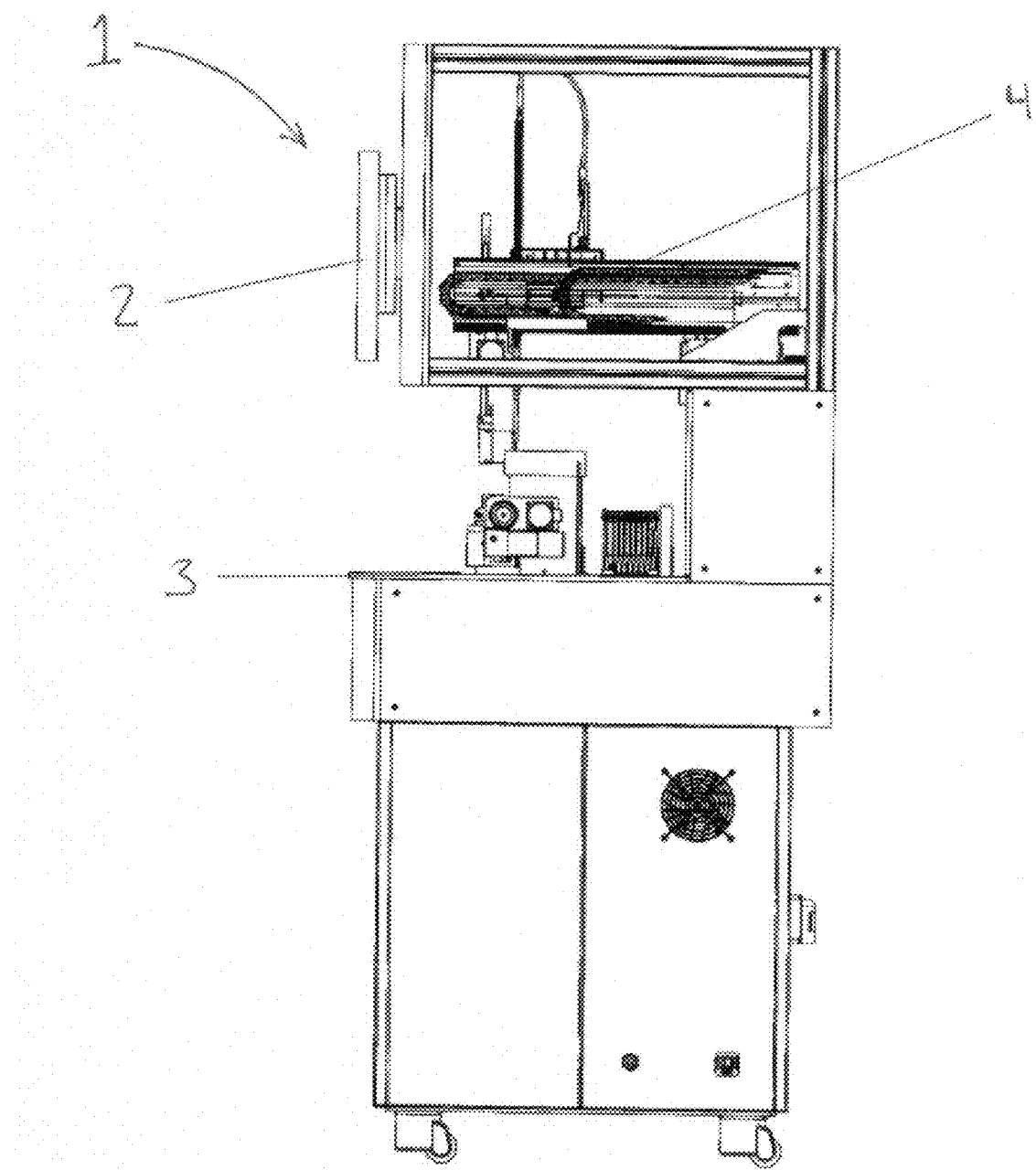
FIG. 3 is a side view of a machine for processing samples according to one embodiment of the invention.

FIG. 3 illustrates the machine 1 comprising a sample-handling robot 4. The sample-handling robot 4 includes an operation head 13, and a verification head 5. Here, the verification head 5 is a barcode reader mechanically coupled to a rack and pinion system. The machine further includes an operation platform 3 having a first station 7 for receiving a sample container and a second station 8 for transferring an aliquot of sample liquid to a testing vial. A waste receptacle 9 is provided for receiving tips and liquids as waste.

Figure 4:
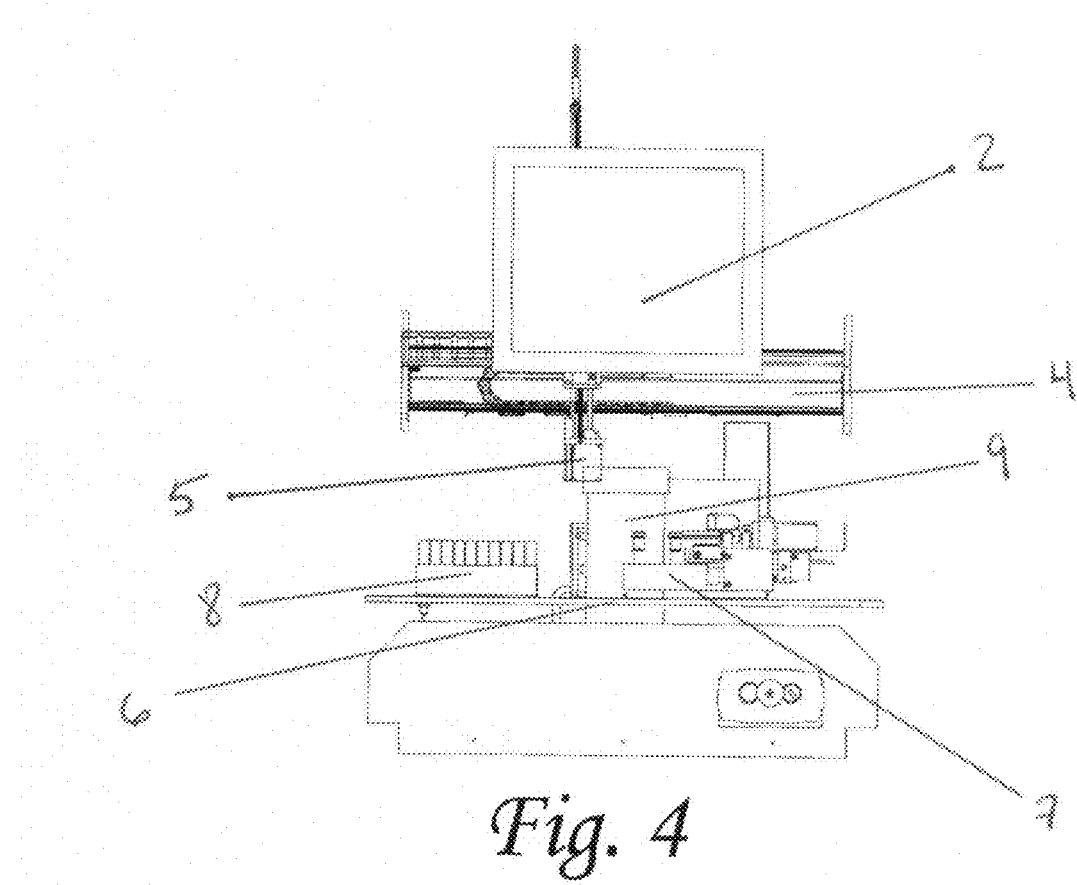
FIG. 4 is a front view of a portion of the machine according to one embodiment of the invention where a sample-handling robot is provided.

FIG. 4 illustrates a portion of the machine including a monitor 2, a sample handling robot, and an operation platform 3, 6 from a front view. The operation platform 3 includes a first station 7 for receiving a sample container and a second station 8 for transferring an aliquot of sample liquid to a testing vial. The operation platform 3 further includes a waste receptacle 9, and a tip station 12. The sample-handling robot 4 includes an operation head 13 and a verification head 5. The verification head 5 is a barcode reader mechanically coupled to a rack and pinion system.

Figure 5:
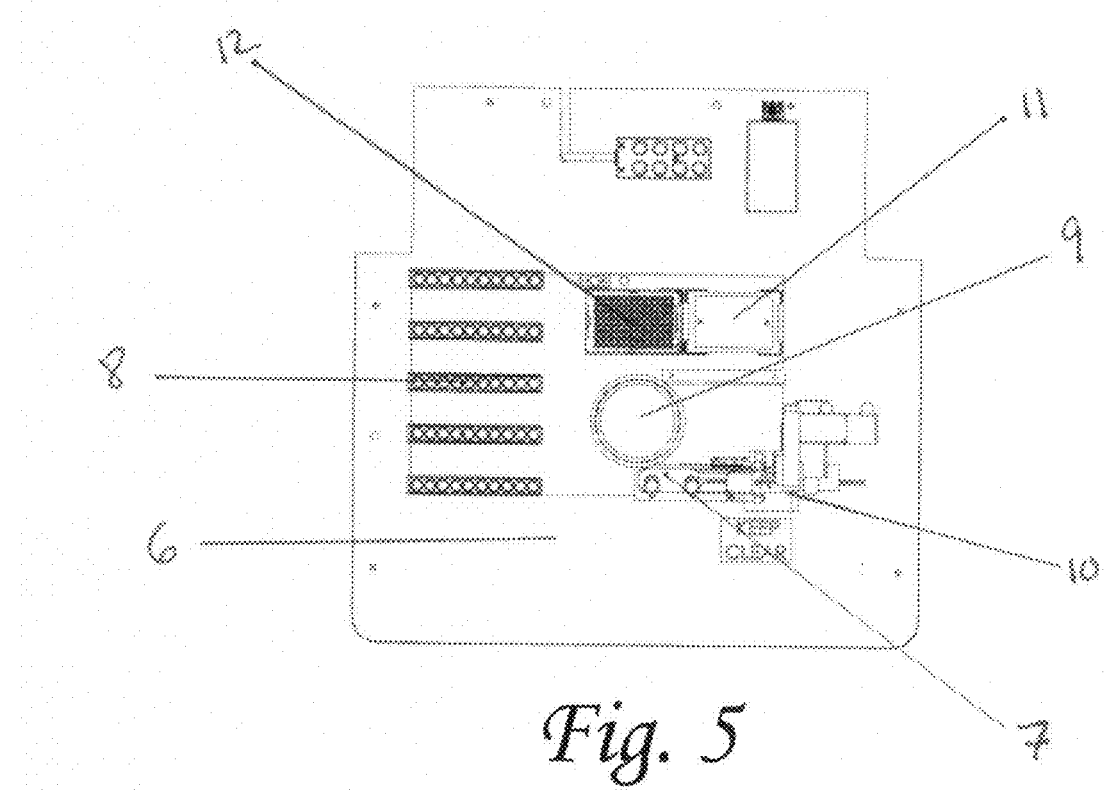
FIG. 5 is a top view of an operation platform according to one embodiment of the invention.
Figure 6:
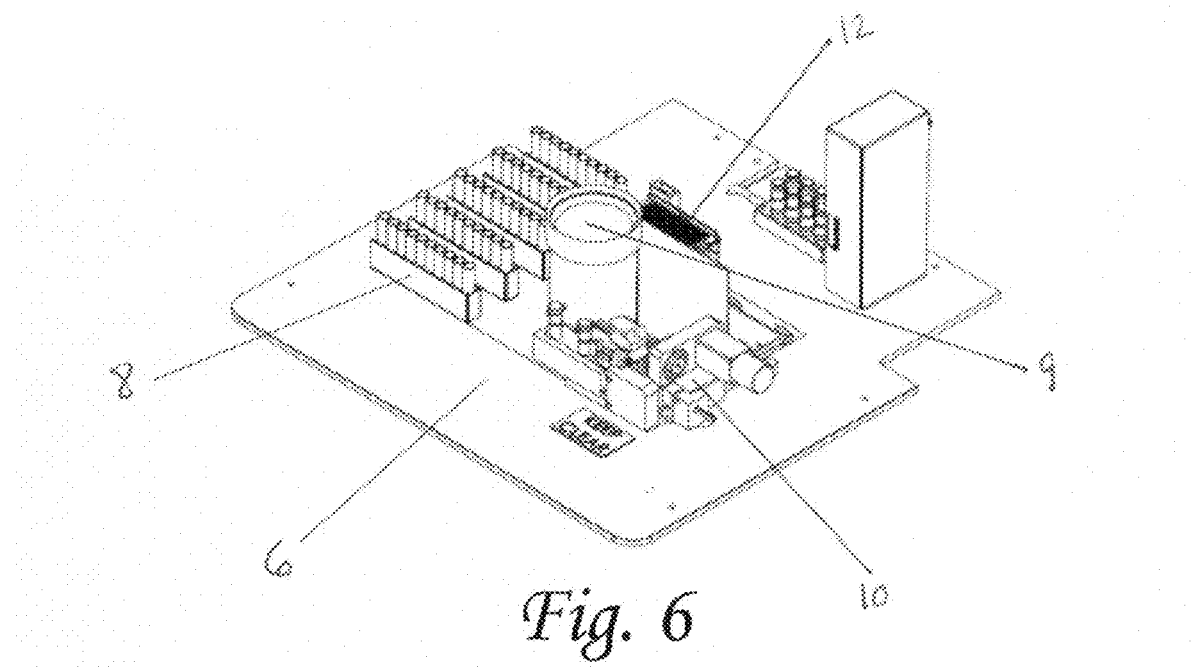
FIG. 6 is a perspective view of an operation platform according to one embodiment of the invention.

FIGS. 5-6 illustrate a top and perspective view, respectively, of the operation platform 6 3. The operation platform 3, 6 comprises a first station 7 for receiving a sample container, and a second station 8 for transferring an aliquot of sample liquid to a testing vial. The operation tray further comprises a tip station 12, and one or more waste receptacle 9s. A first waste receptacle 9 can be provided for the collection of waste tips and sample compositions. A second waste system can include a waste tray and a line for washing or purging the tubing 18 and pipette member 17 of the sample handling robot. The testing vials are positioned in rows, the rows spaced apart by a distance greater than the width of the verification head 5. In a preferred embodiment, the rows can be separated by a distance greater than the width of the verification head 5 and focal length of the barcode reader, such that the verification head 5 can translate between the rows and read an identification member of each testing vial. The first station 7 further includes a lid opening device 10 for mechanically opening the lid of a sample container.

Figure 7:
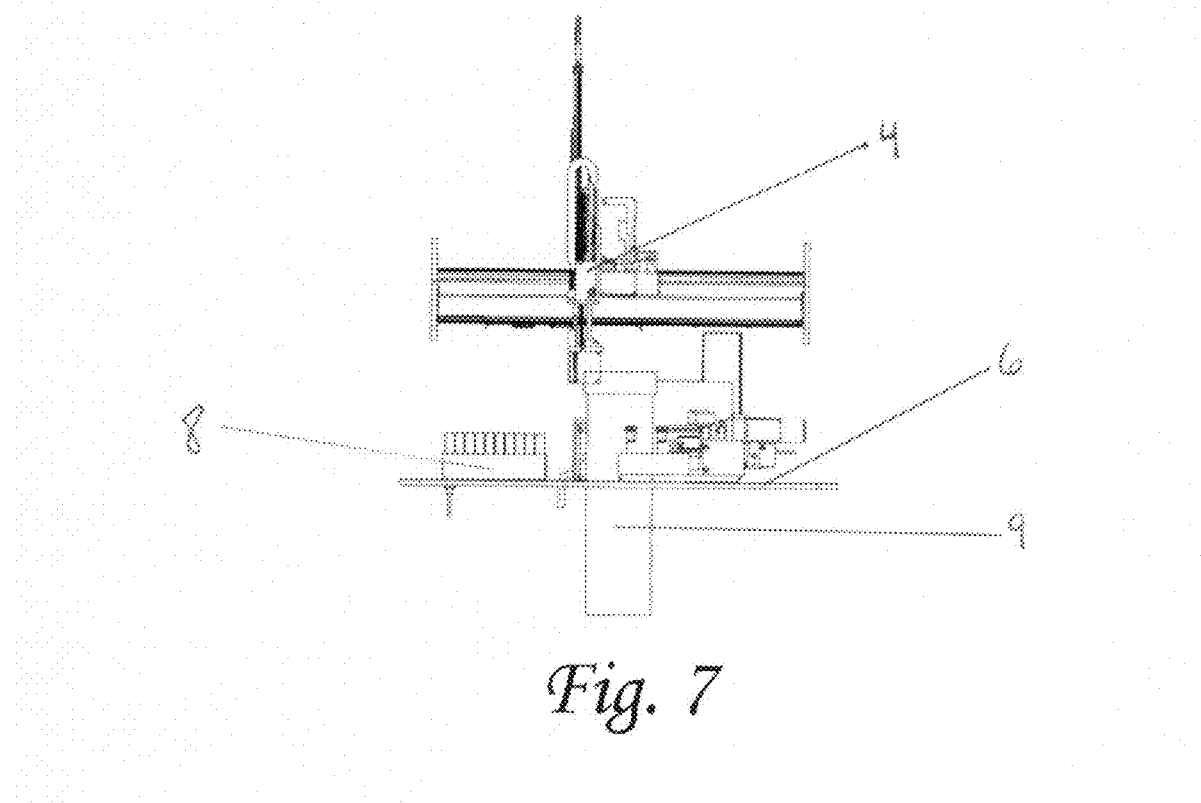
FIG. 7 is a front view of a sample-handling robot and operation platform according to an embodiment of the invention.

FIG. 7 further illustrates a portion of the machine, where the waste receptacle 9 is disposed through the operation platform 3, 6. The waste receptacle 9 can be configured to receive a waste can or other collection member, such that the waste tips can be collected for disposal. Where the samples include hazardous waste, the collection member can be a hazardous waste collection member.

Figure 8:
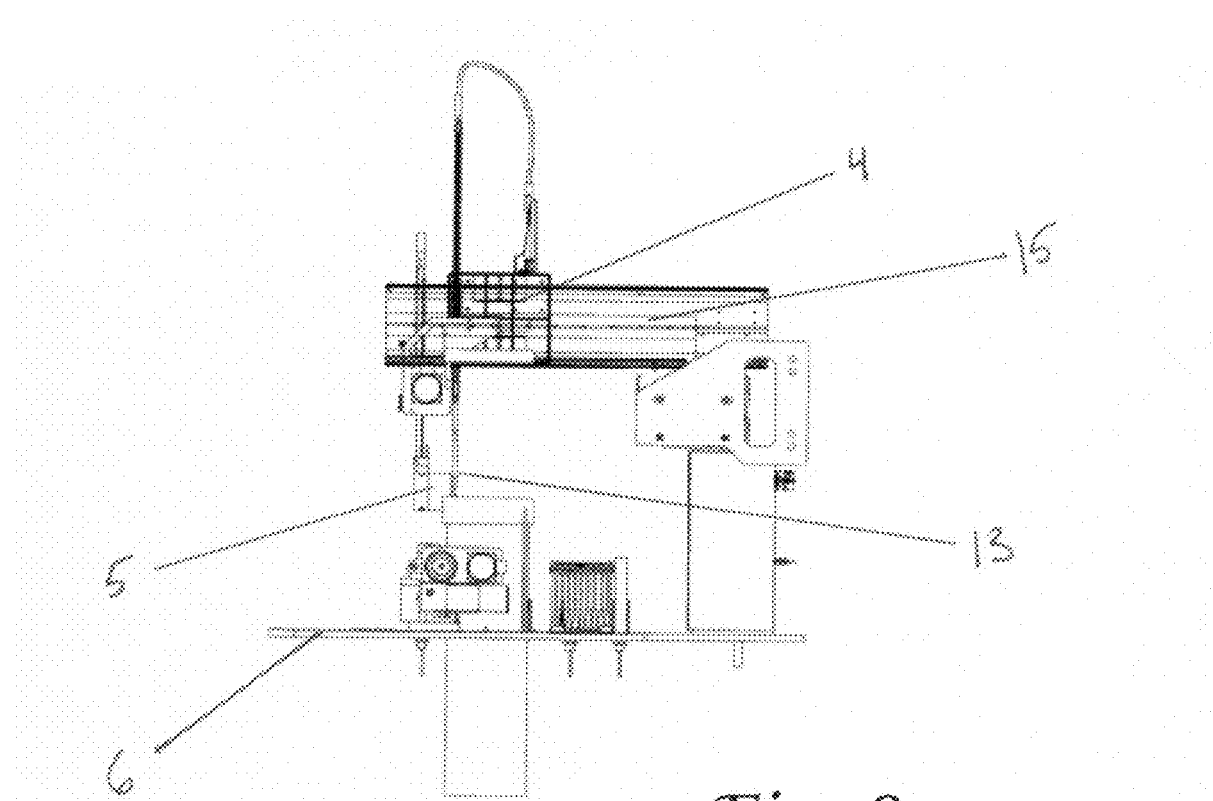
FIG. 8 is a side view of a sample-handling robot and operation platform according to an embodiment of the invention.

FIG. 8 is a side view illustrating a portion of the machine including a sample-handling robot 4 having an operation head 13 and a verification head 5. The sample-handling robot 4 is positioned above an operation platform having a first station 7 for receiving a sample container and mechanically-opening a lid of the sample container. The operation platform 3, 6 further comprises a waste receptacle 9, and a tip station 12.

Figure 9:
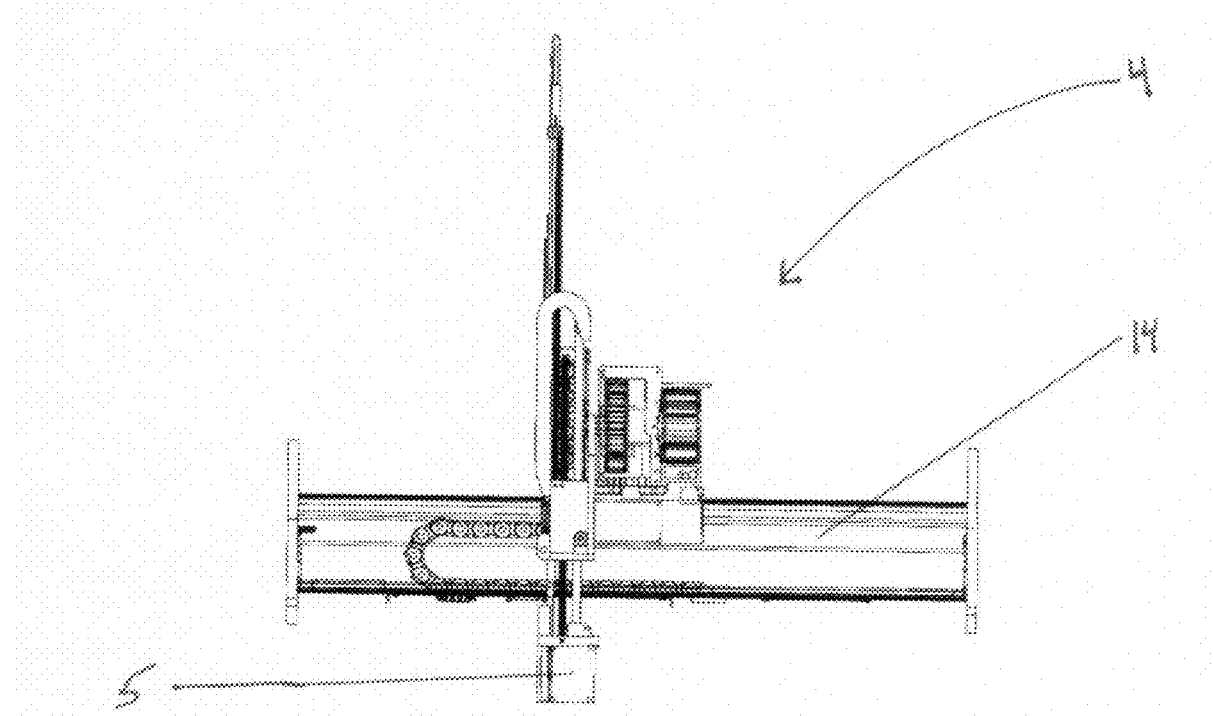
FIG. 9 is a front view of a sample-handling robot having an operation head and a verification head according to one embodiment of the invention.
Figure 10:
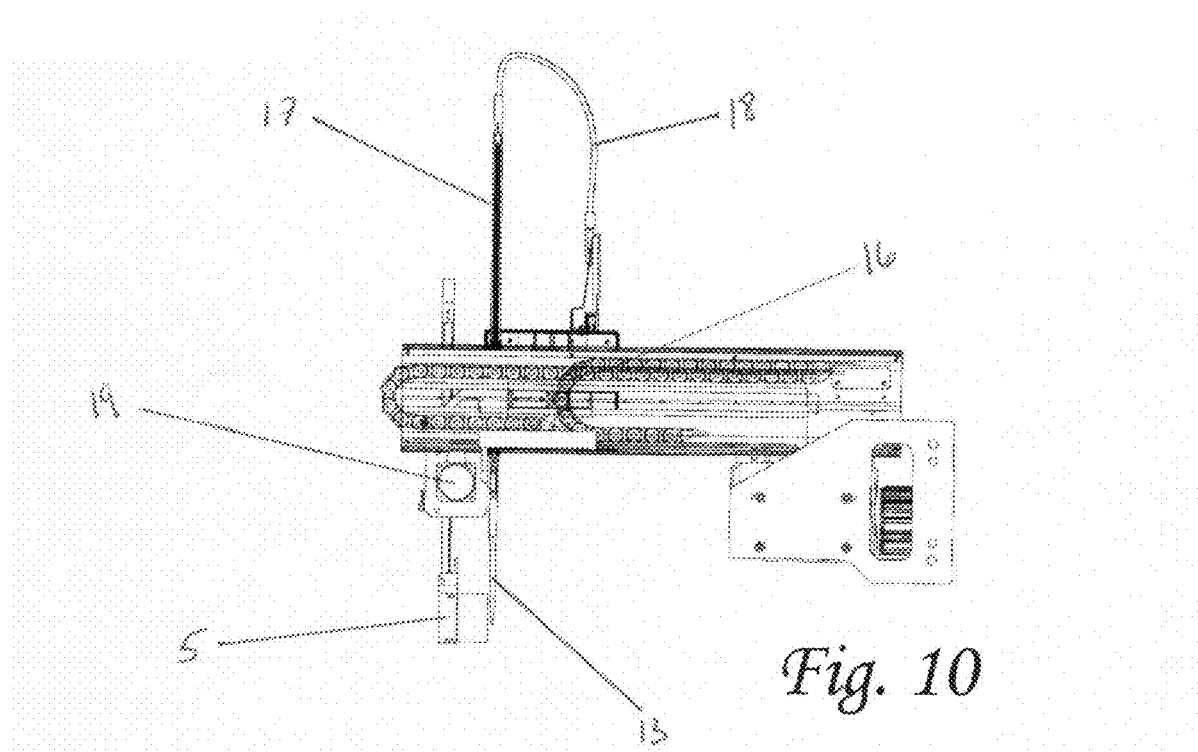
FIG. 10 is a side view of a sample-handling robot having an operation head and a verification head according to one embodiment of the invention.

FIGS. 9-10 illustrate a sample-handling robot 4 comprising a horizontal support bar 14 for positioning the sample-handling robot 4 along an x-axis, a distal support bar 15 for positioning the sample-handling robot 4 along a y-axis, an operation head 13 capable of translating in a vertical direction along a z-axis, and a verification head 5 mechanically coupled to a rack and pinion system 19 for vertically translating the verification head 5 along a z-axis. The horizontal and distal support bar 15s each comprise a track and drive mechanism 16, 21, such that the sample handling robot can translate to any coordinate position within an xy-plane. The track may further include one or more rods or slots for maintaining the position of the robot within the xy-plane.

Figure 11:
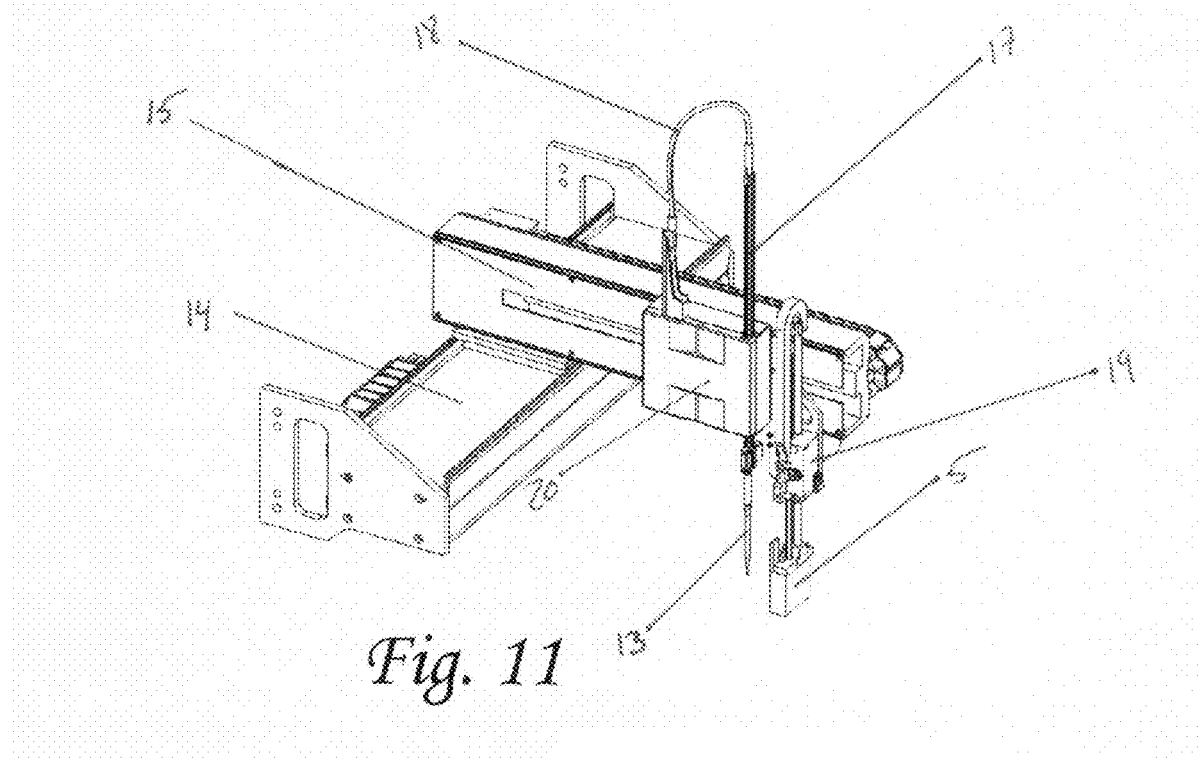
FIG. 11 is a perspective view of a sample-handling robot having an operation head and a verification head according to one embodiment of the invention where the verification head is adapted for vertical translational movement.
Figure 12:
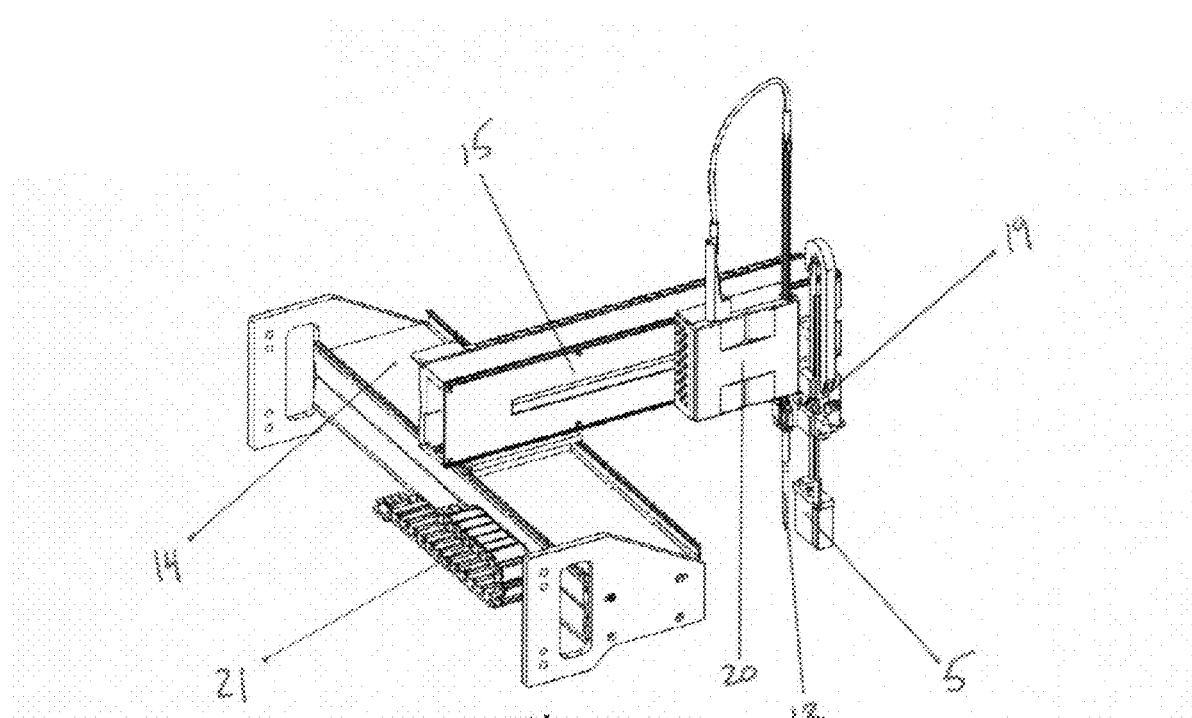
FIG. 12 is a perspective view of a sample-handling robot having an operation head and a verification head according to one embodiment of the invention where the verification head is adapted for vertical translational movement.

FIGS. 11-12 illustrate a sample-handling robot 4 including a horizontal support bar 14 for positioning the sample handling robot along an x-axis, a distal support bar 15 for positioning the sample handling robot along a y-axis, an operation head 13 connected to a stepper motor 20 capable of translating in a vertical direction along a z-axis, and a verification head 5 mechanically coupled to a rack and pinion system for vertically translating the verification head 5 along a z-axis. The verification head 5 comprises a barcode reader connected to a motor-driven vertical translating bar. The verification head 5 is adapted to read a barcode and send corresponding data to a computer database.

Figure 13:
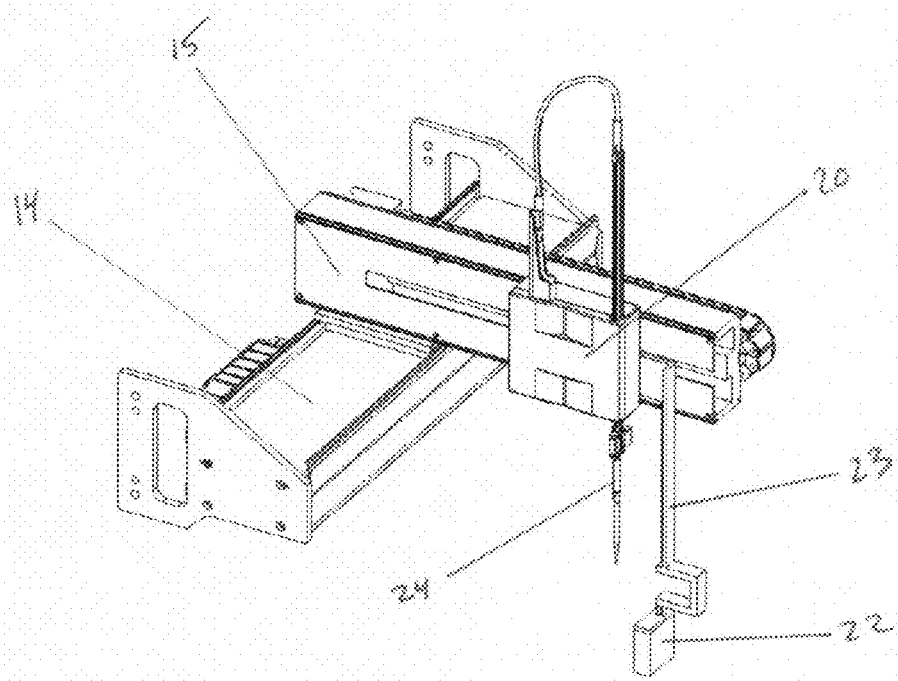
FIG. 13 is a perspective view of a sample-handling robot having an operation head and a verification head according to one embodiment of the invention where the verification head is fixedly configured at a distance above the operation platform.
Figure 14:
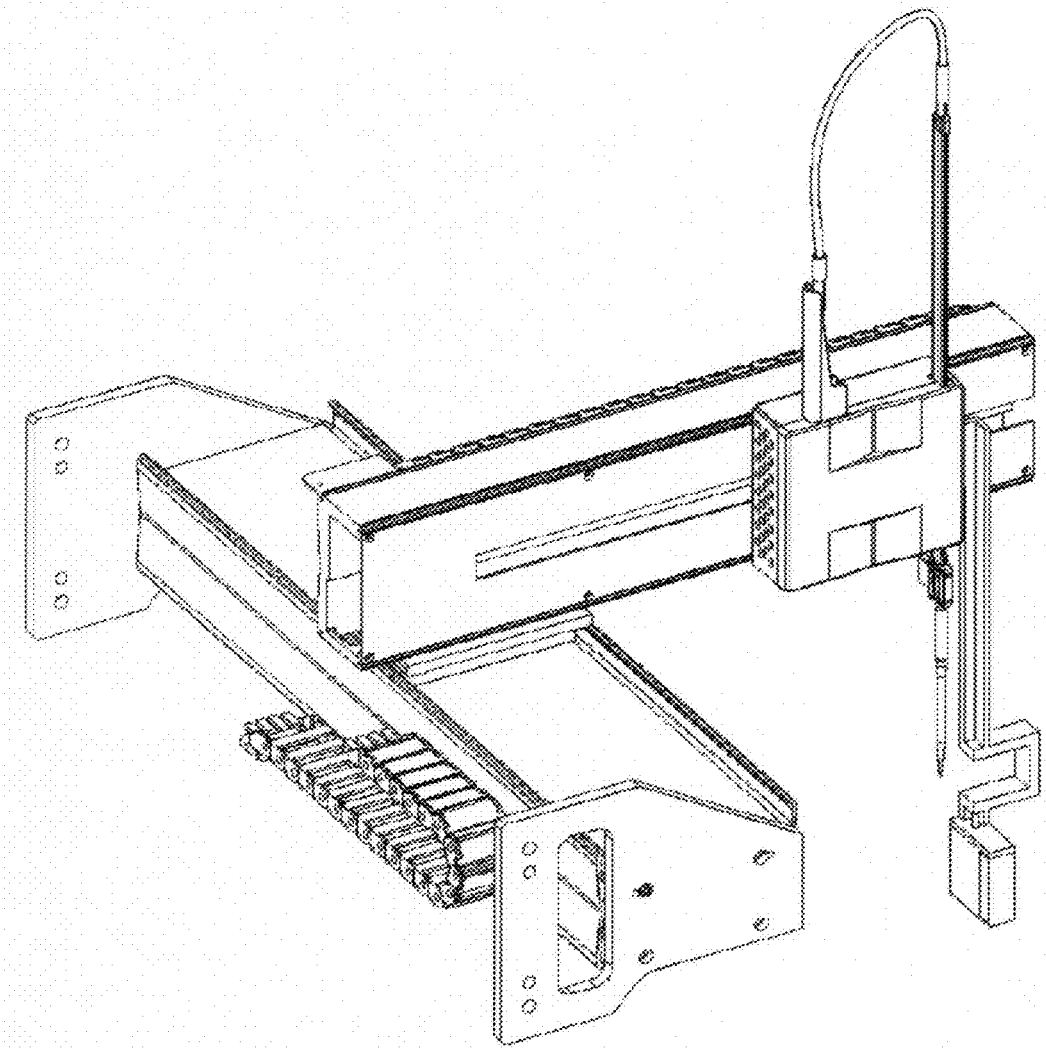
FIG. 14 is a perspective view of a sample-handling robot having an operation head and a verification head according to one embodiment of the invention where the verification head is fixedly configured at a distance above the operation platform.

FIGS. 13-14 illustrate a sample-handling robot 4 including a horizontal support bar 14 for positioning the sample handling robot along an x-axis, a distal support bar 15 for positioning the sample handling robot along a y-axis, an operation head 24 connected to the robot by a stepper motor 20, the operation head 24 is capable of translating in a vertical direction along a z-axis using the stepper motor 20, and a verification head 23 fixedly positioned at a distance below the distal support bar 15. The verification head 23 comprises a barcode reader 22 connected to a motor-driven vertical translating bar. The verification head 23 is adapted to read a barcode and send corresponding data to a computer database.

The machines described in the foregoing detailed description each include one or more verification heads for reading and processing information, such as information associated with an identification member of a sample container. The verification head is generally attached to a computer or similar device for processing the information read by the verification head. The information processed can be compiled into one or more reports, the reports comprising analysis of testing data, and various other data such as chain of custody data. A report can be generated from the data read and processed by the verification head, and can further include analytical testing results where the sample is tested using an analytical testing machine. It is therefore intended to be within the spirit and scope of the invention to include reports and methods for reporting results, wherein at least a portion of the results includes information read and processed by the verification head.

The above examples are set forth for illustrative purposes and are not intended to limit the spirit and scope of the invention. One having skill in the art will recognize that deviations from the aforementioned examples can be created which substantially perform the same tasks and obtain similar results.

What is claimed is:

1. A method for maintaining chain of custody of a sample throughout a processing sequence conducted within a laboratory sampling apparatus, the method comprising:
    (a) placing a first article into a first station comprising a lid opening device, the first article including a first identification member;
    (b) translating a verification head from a verification-home position to a position proximate to the first article;
    (c) reading the first identification member of the first article;
    (d) returning the verification head from the position proximate to the first article to the verification-home position;
    (e) using the lid opening device, rotationally actuating a lid of the first article to an open position;
    (f) translating an operation head from an operation-home position to a first operation position proximate to the first article;
    (g) performing a first operation on the first article using the operation head;
    (h) translating the operation head from the first operation position proximate to the first article to the operation-home position;
    (i) using the lid opening device, rotationally actuating the lid of the first article to a closed position;
    (j) translating the verification head and the operation head to a second station having a second article, the second article including a second identification member;
    (k) translating the verification head from the verification-home position to a position proximate to the second article;
    (l) reading the second identification member of the second article;
    (m) translating the verification head from the position proximate to the second article to the verification-home position;
    (n) translating the operation head from the operation-home position to a second operation position proximate to the second article;
    (o) performing a second operation on the second article using the operation head;
    (p) translating the operation head from the second operation position proximate to the second article to the operation-home position.

2. The method of claim 1, wherein at least one of said first and second identification members is a bar code.

3. The method of claim 1, wherein at least one of said first and second identification members is an alpha-numeric label.

4. The method of claim 1, wherein at least one of said first and second identification members is a radio frequency identification tag.

5. The method of claim 1, wherein the first and second articles are containers.

6. The method of claim 5, wherein the first article contains a sample.

7. The method of claim 6, wherein the sample is a biological sample.

8. The method of claim 1, wherein the first operation is an aspiration.

9. The method of claim 1, wherein the second operation is a dispensing operation.

10. The method of claim 1, further comprising the steps of:
    (q) translating the verification head and the operation head to a third station having a third article, the third article including a third identification member;
    (r) translating the verification head from the verification-home position to a position proximate to the third article;
    (s) reading the identification member of the third article;
    (t) translating the verification head from the position proximate to the third article to the verification-home position;
    (u) translating an operation head from the operation-home position to a third operation position proximate to the third article;
    (v) performing a third operation on the third article using the operation head;
    (w) translating the operation head from the third operation position proximate to the third article to the operation-home position.

11. The method of claim 6, further including the steps of:
    (q) analyzing the sample contained in one or more testing vials, and
    (r) generating test results, wherein the test results at least partially include data received from the verification head.

12. An article comprising: a test result report at least partially derived from a sample evaluated according to the method of claim 11.

13. An apparatus, comprising:
a sample handling robot having an operation head and a verification head, and
an operation platform,
the operation platform comprising a lid opening device adapted to rotationally actuate a lid of a sample container between a closed position and an open position such that the lid is opened and closed by the lid opening device for preventing cross-contamination;
the verification head including one of: a barcode reader, an optical character recognition scanner, or a radiofrequency identification tag reader,
wherein the operation head is adapted to perform a mechanical function, and
wherein the verification head is adapted to read and process information.

14. The apparatus of claim 13, wherein the verification head is mechanically coupled to the sample-handling robot by a rack and pinion system.

15. The apparatus of claim 13, wherein the operation platform includes a first station for receiving a sample, a second station for transferring an aliquot of the sample to a testing vial, a waste station having a waste receptacle, and a tips station.

16. The apparatus of claim 15, wherein the first station further comprises the lid-opening device.

17. The apparatus of claim 16, further comprising a secondary robot for transferring a sample container from a sample container rack to the first station.

18. The apparatus of claim 17, wherein the secondary robot includes an second operation head, the second operation head including a first gripping member and a second gripping member for securing and transporting an article.

19. The apparatus of claim 18, wherein the secondary robot further includes a second verification head, the second verification head adapted to vertically translate to a position proximate to an article, and read an identification member positioned on an exterior surface of the article.

20. The apparatus of claim 13, further comprising a second sample-handling robot, the second sample-handling robot comprising a second operation head and a second verification head.

* * * * *